US 6,524,341 B2

(12) United States Patent
Läng et al.

(10) Patent No.: US 6,524,341 B2
(45) Date of Patent: Feb. 25, 2003

(54) TELESCOPIC VERTEBRAL PROSTHESIS

(75) Inventors: Bruno Läng, Horriswil (CH); Alfred Benoit, Lengnau (CH)

(73) Assignee: Synthes (USA), Paoli, PA (US)

(*) Notice: Subject to any disclaimer, the term of this patent is extended or adjusted under 35 U.S.C. 154(b) by 0 days.

(21) Appl. No.: 09/833,665

(22) Filed: Apr. 13, 2001

(65) Prior Publication Data

US 2002/0161441 A1 Oct. 31, 2002

Related U.S. Application Data

(63) Continuation of application No. PCT/CH98/00441, filed on Oct. 15, 1998.

(51) Int. Cl.$^7$ ................................................. A61F 2/44
(52) U.S. Cl. ..................................................... 623/17.15
(58) Field of Search ....................... 606/61; 623/17.11, 623/17.13, 17.15, 17.16

(56) References Cited

U.S. PATENT DOCUMENTS

| | | | |
|---|---|---|---|
| 4,554,914 A | | 11/1985 | Kapp et al. |
| 4,657,550 A | * | 4/1987 | Daher ........................ 606/61 |
| 4,892,546 A | | 1/1990 | Kotz et al. |
| 5,330,535 A | | 7/1994 | Moser et al. |
| 5,571,192 A | * | 11/1996 | Schonhoffer ............... 606/61 |
| 5,702,453 A | | 12/1997 | Rabbe et al. |
| 5,702,455 A | * | 12/1997 | Saggar ..................... 623/17.15 |
| 5,723,013 A | | 3/1998 | Jeanson et al. |
| 5,776,198 A | | 7/1998 | Rabbe et al. |
| 6,015,436 A | | 1/2000 | Schönhöffer |
| 6,086,613 A | * | 7/2000 | Camino et al. ............ 623/17.16 |
| 6,176,881 B1 | | 1/2001 | Schär et al. |

FOREIGN PATENT DOCUMENTS

| | | |
|---|---|---|
| DE | 27 50 648 A1 | 5/1979 |
| DE | 302 39 42 A1 | 1/1982 |
| DE | 196 04 246 A1 | 8/1996 |
| DE | 196 22 827 A1 | 12/1997 |
| EP | 0 290 767 A1 | 11/1988 |
| WO | WO 96/17564 | 6/1996 |

* cited by examiner

Primary Examiner—Eduardo C. Robert
(74) Attorney, Agent, or Firm—Pennie & Edmonds LLP

(57) ABSTRACT

The present invention is directed to a vertebral bone prosthetic device comprising an interior body, provided with an outer surface and a first coupling element thereon, and an exterior hollow body with a bore therein extending along a central axis, with the interior body being configured and dimensioned to be slidably received by the exterior body along the central axis, and provided with an interior surface and an exterior surface, the interior surface having a groove. The device also comprises a fixation ring having inner and outer surfaces, with the inner surface having a second coupling element thereon. The fixation ring is configured and dimensioned to be received within the groove of the exterior body for rotational movement about the central axis of the exterior body. Rotation of the fixation ring results in engagement of the first and second coupling elements to thereby prevent relative sliding movement between the interior and exterior bodies. Also, the fixation ring is rotatable between first second positions, the first position disengaging the coupling elements and allowing relative sliding movement and the second position engaging the coupling elements and blocking relative sliding movement.

18 Claims, 2 Drawing Sheets

TELESCOPIC VERTEBRAL PROSTHESIS

CROSS-REFERENCE TO RELATED APPLICATIONS

This application is a continuation of the U.S. national stage designation of copending International Patent Application PCT/CH98/00441, filed Oct. 15, 1998, the entire content of which is expressly incorporated herein by reference thereto.

FIELD OF THE INVENTION

The present invention concerns a device for replacing vertebrae from the spine, and in particular to a length adjustable prosthesis for replacing vertebrae.

BACKGROUND OF THE INVENTION

If a vertebra becomes diseased or suffers damage it must be removed from the spinal column. Some spacer implants for replacement of defective vertebra are known from the related art. The implants generally have mutually displaceable components, a mechanism to adjust the length of the implant, and special end plates that serve to anchor the implant into adjoining and intact vertebrae.

Such implants are known, for example, from U.S. Pat. No. 4,554,914 to Kapp et al., which discloses a vertebral prosthesis having a pair of support elements and fasteners. The pair of support elements are length adjustable and are inserted into a cavity formed by the removal of a defective vertebra. An expansion device is inserted between opposing surfaces of the adjacent intact vertebrae to force apart the adjacent vertebrae, until the normal height of the vertebra to be replaced is restored. The pair of support elements are adjusted to fit the axial gap, and support the adjoining vertebrae. Once set, fluid and hardening material is inserted around the length-adjusted support elements, to embed them and fixate the adjusted length of the prosthesis.

The support elements in Kapp consist of a bushing having a threaded interior surface, and screws fitting into the threads. Moreover, the bushings are conically tipped at the outer end whereas the screws are wedge-shaped at their outer end. Expanding the support elements in the cavity between the vertebrae causes the outer end of bushings and screws to penetrate the adjacent vertebrae. The conical tips allow rotating the bushing, while the outer wedge-shaped screw ends preclude the screws from rotating, and accordingly length adjustment of the support element can be carried out by rotating the bushing. The fasteners consist of two elongated plates having recesses and screw-holes. These plates are placed on both sides of the spinal column against the dorsal vertebral eminences and screwed into them. The screw holes in the plates are configured in such manner that the screws pass through the dorsal vertebral eminences and as a result fixate the spinal column in the region of the vertebral prosthesis. This known vertebral prosthesis suffers from the drawback that the support elements provide adequate stability only in the case of precise axial loading. Furthermore the insertion of two such support elements into the cavity between the adjoining healthy vertebrae and their length adjustment using the threads is time consuming.

Another device for the prosthetic replacement of a vertebra is known from German Patent DE 30 23 942 to Keller. This known device comprises two members each having a support end for setting up against the adjacent vertebral body and being coaxially telescoping. The telescoping sections of these members comprise a rod at the first member and a complementary bore at the other member. The rod and the bore are provided with an oval cross-section that allows axial displacement of the rod within the bore, if the longer axes of the oval cross-sections are in alignment. If the two members are rotated about the longitudinal axis by 90° relative to each other, the threads at the rod engage with the threads in the bore to fix axial movement between the two members. A disadvantage of this known device is that both members must be rotated relative to each other together with the plates that serve as support ends. Thus, the support ends which are in contact with the adjacent vertebrae may damage the healthy vertebrae as the plate is rotated.

Therefore, a need exists for a stable, length-adjustable vertebral prosthesis, which is easily handled in surgery and which restores and maintains the biomechanical and physiological properties of the spinal column despite the removal of one or more defective vertebrae.

SUMMARY OF THE INVENTION

The present invention is directed to a vertebral bone prosthetic device comprising an interior body, provided with an outer surface and a first coupling element thereon, and an exterior hollow body with a bore therein extending along a central axis, with the interior body being configured and dimensioned to be slidably received by the exterior body along the central axis, and provided with an interior surface and an exterior surface, the interior surface having a groove. The device also comprises a fixation ring having inner and outer surfaces, with the inner surface having a second coupling element thereon. The fixation ring is configured and dimensioned to be received within the groove of the exterior body for rotational movement about the central axis of the exterior body. Rotation of the fixation ring results in engagement of the first and second coupling elements to thereby prevent relative sliding movement between the interior and exterior bodies. Also, the fixation ring is rotatable between first second positions, the first position disengaging the coupling elements and allowing relative sliding movement and the second position engaging the coupling elements and blocking relative sliding movement.

In an exemplary embodiment, the invention comprises two hollow cylinders, which can be mutually displaced and telescoped into each along a central axis, and a hollow cylindrical affixation ring which is mounted concentrically to the central axis of the two hollow cylinders. The affixation is ring supported in a groove on the inside surface of the outer hollow cylinder such that the affixation ring is free to rotate about the central axis. Sectorial elevations are present on the outside surface of the inner hollow cylinder, in the form of a pitchless thread, and sectorial recesses matching the sectorial elevations are present within the bore of the affixation ring. Engagement of the sectorial elevations and recesses provides axial locking of the two hollow cylinders to one another.

In a preferred embodiment, the diameter of the hollow inner ring and the affixation ring are such as to allow mutual axial displacement of the inner and outer hollow cylinders. In addition, the affixation ring has three sectors having recesses, and the inner hollow cylinder has three sectors having elevations, with each sector subtends an angle of 60°. Other sectors, also subtending an angle of 60° are situated between the sectors fitted with elevations and recesses. Within the other sectors, elevations are absent from the hollow inner cylinder, and recesses are absent from the affixation ring. The elevations and recesses may be engaged in a first angular position (position A), wherein the position of the affixation ring and the inner hollow cylinder are mutually locked, in the direction of the central axis. In a second angular position (position B), the elevations and recesses of the inner hollow cylinder and the affixation ring, respectively, are disengaged, to produce two hollow bodies which are mutually and freely displaceable, in the direction of the central axis. End plates are mounted to the free ends of the inner and outer hollow cylinders. The end plates have a diameter larger than that of the inner and of the outer hollow cylinder. The free surfaces of these end plates will rest against the adjacent vertebrae. The free surfaces of said end plates are further fitted with three-dimensional structures consisting of conical or pyramidal tips. The tips dig into the surface of the adjacent vertebrae, when the present invention is inserted within the evacuated vertebral space and spread apart to secure the prosthesis.

Both hollow cylinders maybe crossed end to end along the central axis by a bore. The cavity, so subtended, may be filled with bone chips to enhance osteointegration of the two adjacent vertebrae to the present invention. To enhance growth of adjacent vertebra onto the implant, the end plates of the present invention which adjoin the vertebra may be fitted with perforations. Inside the outer hollow cylinder a channel in the bore runs in the direction of the central axis. A beak or tab on the inner hollow cylinder engages the channel to secure the two hollow cylinders against rotation. In this manner, the hollow cylinders are precluded from mutual rotation when the affixation ring is rotated.

An offset maybe present on the outside surface of the affixation ring, which can be displaced in such manner inside a corresponding clearance to allow rotation of the ring between position A and position B. Further the beak of the affixation ring when in position A rests against one sidewall of the clearance and when in position B rests against the other sidewall. The lateral stops, so implemented for the offset at the affixation ring, allow for easily ascertaining the first angular position of the affixation ring, in which both hollow cylinders are axially locked in position, or the second angular position of the affixation ring, wherein the two hollow cylinders are mutually axially displaceable. To secure the affixation ring in a selected position, an axially projecting, V-shaped elevation may be present at the offset, which detents into corresponding flutings in the clearance, whereby the affixation ring is detachably locked in positions A or B.

Essentially, the general advantage offered by the present invention include high stability, which is achieved under axial load, and that the adjacent vertebrae may knit over an adequately large cross-section of the prosthesis. Additionally, when the present invention is inserted into the evacuated vertebral space, the device is extended by expansion tongs until the end plates come to rest against the adjoining, healthy vertebrae, and the tips on the end plates penetrate sufficiently deeply into these vertebrae. For that purpose, the affixation ring can be rotated, beforehand, into the second angular position (i.e., position B). Once the implant has been adjusted to the required length, the affixation ring is rotated into its first angular position (position A) by a bar, which is insertable into a bore in the affixation ring especially provided for that purpose. In this manner, the prosthesis device is locked at the desired length. This lengthwise locking of the implant assures easy handling during the device implantation.

BRIEF DESCRIPTION OF THE DRAWINGS

Preferred features of the present invention are disclosed in the accompanying drawings, wherein similar reference characters denote similar elements throughout the several views, and wherein.

DETAILED DESCRIPTION OF THE PREFERRED EMBODIMENTS

Figure 1:
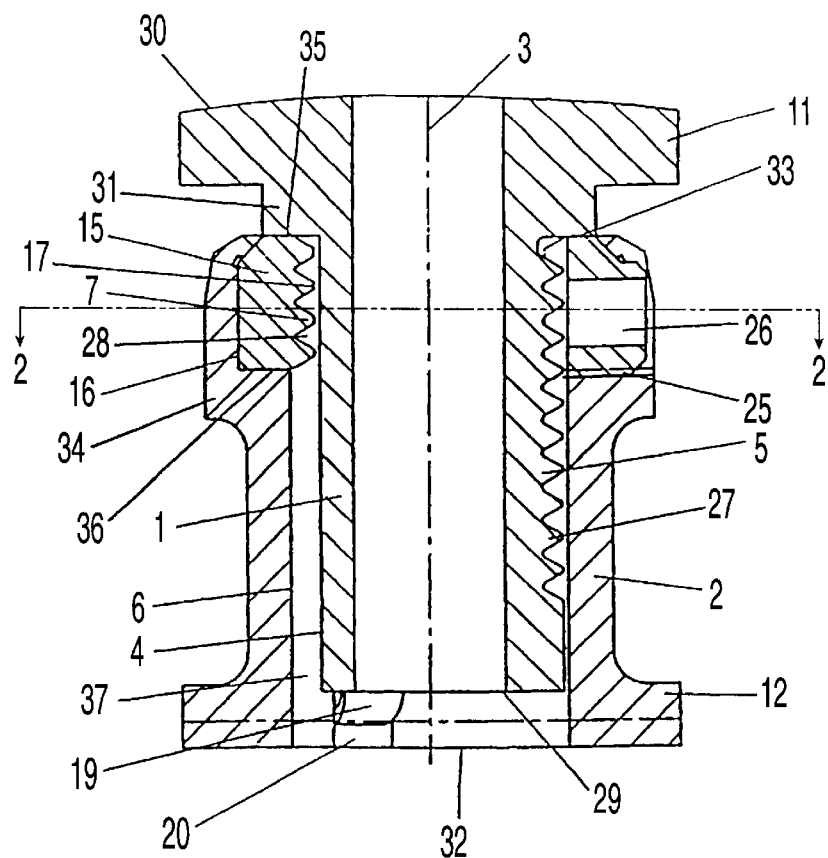
FIG. 1 is a longitudinal sectional view of one embodiment of the vertebral replacement device according to the present invention, with the device at its minimum height, and the coupling elements disengaged.

For convenience, the same or equivalent elements in the various embodiments of the invention illustrated in the drawings have been identified with the same reference numerals. Further, in the description that follows, any reference to either orientation or direction is intended primarily for the convenience of description and is not intended in any way to limit the scope of the present invention thereto.

FIG. 1 shows a longitudinal section of an exemplary embodiment of the device of the present invention. This device comprises an inner hollow body 1, an outer hollow body 2, and an affixation ring 15. The inner hollow body 1 and outer hollow body 2 are configured concentrically around a central axis 3. The inner hollow body 1 is displaceable within the cavity 37 of the outer hollow body 2 along this central axis 3. In this manner, the two hollow bodies 1 and 2 are mutually telescoping. In the embodiment shown in FIG. 1, the inner hollow body 1 is inserted into the cavity of the outer hollow body 2, whereby the device so shown is of minimum height. The inner hollow body 1 consists at its upper end 30 of a polygonal end plate 11, with an adjoining circular-cylindrical milling 31, and a cylindrical part having an outside surface 4. The outside surface 4 is fitted with elevations 27 which act as first coupling elements 5.

Figure 2:
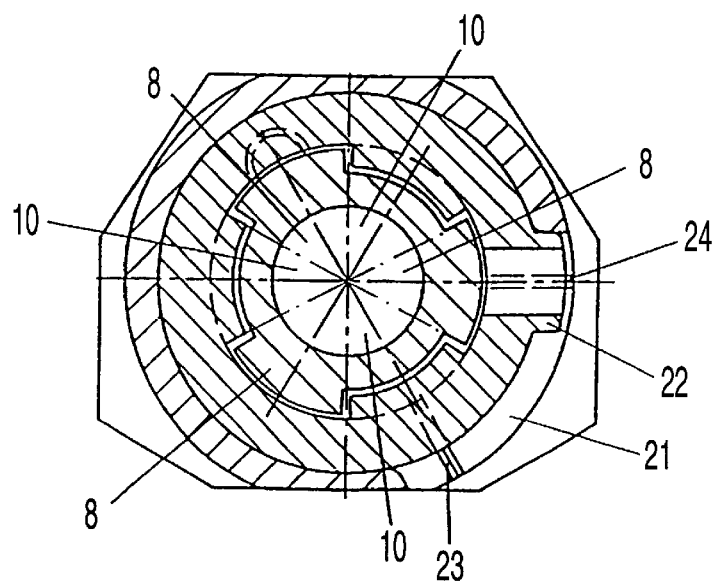
FIG. 2 is a cross-sectional view through line 2—2 of FIG. 1.

Referring to FIGS. 1 and 2, these elevations 27 are present on the outside surface 4 in sectors 8 having an angle of 60°. Other sectors 10 on the outside surface 4 lack elevations 27 and are situated between the sectors 8 with elevations 27. These other sectors 10 also subtend an angle of 60°. The elevations 27 assume the shape and contour of a pitchless thread.

Referring back to FIG. 1, the outer hollow body 2 also comprises a polygonal end plate 12 at its lower end 32, an adjoining circular-cylindrical middle part; and an upper part, also circular-cylindrical, of a larger outer diameter than the middle part near the upper end 33. Cavity 37, concentric with the central axis 3, is of such diameter that the inner hollow body 1 fitted with the first coupling elements 5 is displaceable in the direction of the central axis 3 within this cavity 37. Furthermore, a groove 20 running parallel to the central axis 3 is present in the surface 6 of the outer hollow body 2, and is of such dimensions that a beak or tab 19 at the lower end 29 of the inner hollow body 1 is able to engage this groove 20 to prevent mutual rotation of the two hollow bodies 1 and 2. The axial length of groove 20 is selected in such a way that the inner hollow body 1 is telescopable over the length of the inner hollow body 1 fitted with first coupling elements 5. The affixation ring 15 comprises a second coupling elements 7 and is inserted about the central axis 3 in a groove 16 within surface 6 running concentrically with the central axis 3. The affixation ring 15 is rotatable within the groove 16 to lock the axial position of the inner hollow body 1 relative to the outer hollow cylinder 2. The affixation ring 15 assumes the shape of a cylindrical ring. The inside surface 17 of ring is fitted with recesses 28 which act as second coupling elements 7.

Figure 4:
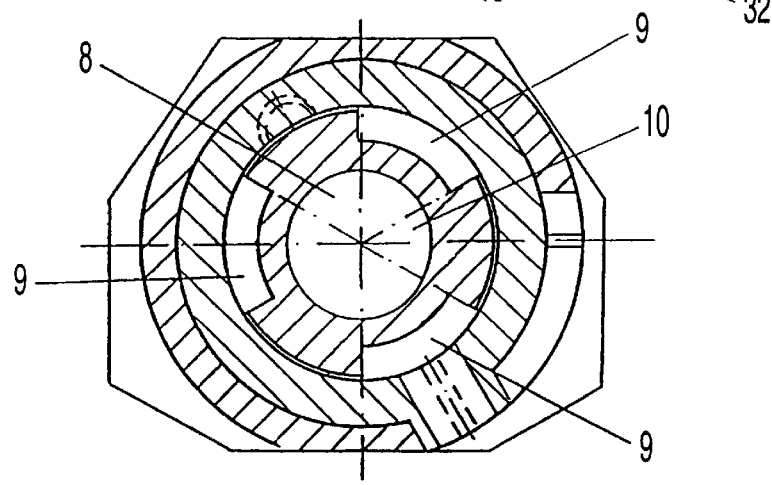
FIG. 4 is a cross-sectional view through line 4—4 of FIG. 3.

Referring to FIGS. 1 and 2, these recesses 28 are configured on the inside surface 17 in sectors 10 subtending an angle of 60°. As best shown in FIG. 4, however, other sectors 9 lack recesses 28 and subtend an angle of 60°. Referring back to FIG. 1, the recesses 28 are in the shape and contour of a pitchless thread matching the elevations 27 at the outside surface 4 of the inner hollow body 1. As described in more detail below, elevations 27 engage recesses 28 in a first position, position A, to prevent relative motion between inner and outer bodies 1, 2. FIGS. 1 and 2 show the first coupling elements 5 on the inner hollow cylinder 1, and the second coupling elements 7 on the affixation ring 15 in position B. In position B, first and second coupling elements 5 and 7, respectively, are disengaged and the hollow body 1 and hollow body 2 are freely displaceable relative to each other in the direction of the central axis 3. In order to more easily set the operating configuration between position A and position B, the affixation ring 15 comprises an offset 22 that engages a clearance 21 in the outer hollow cylinder 2. The dimensions of the offset 22 and the clearance 21 are operably configured to allow rotation of the affixation ring 15 between the positions A and B. Moreover, an axially projecting V-shaped elevation 25 is present at the offset 22, which detents into corresponding flutings 23 and 24 in the clearance 21, to detachably affix the affixation ring into operable position A and B, respectively. The offset 22 also comprises a radial bore 26. A common mandril (not shown) may be inserted into the bore 26 for use as a lever to rotate the affixation ring 15 between position A and position B.

Figure 3:
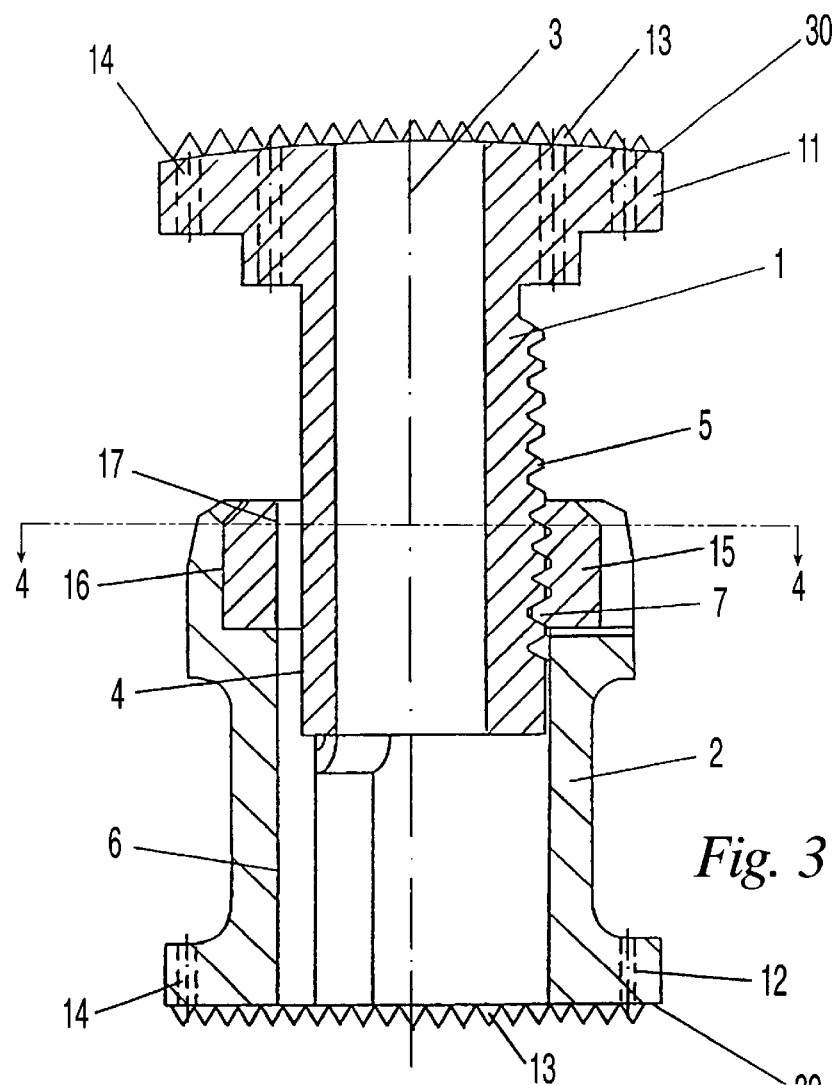
FIG. 3 is a longitudinal sectional view of the device of FIG. 1, with the device at an increased height, the coupling elements engaged, and teeth positioned on the end plates.

FIG. 3 shows another embodiment of the invention, in an extended and locked position. This embodiment differs from the embodiment of FIG. 1, in that conical tips or teeth 13 are present on the end plates, located at the lower end 32 of the outer hollow cylinder 2, and at the upper end 30 of the inner hollow cylinder 1. The tips 13 are able to penetrate the particular adjoining healthy vertebrae. Furthermore, both end plates 11 and 12 are perforated, thereby enhancing bony ingrowth of adjacent vertebrae to the implanted device.

As shown in FIG. 4, the affixation ring 15 appropriately is in operable position A, namely, the coupling elements 5 and 7 are engaged. In operable position A, the recesses 28 and the elevations 27 are geometrically interlocked to prevent mutual displacement of the two hollow bodies 1 and 2 in the direction of the central axis 3.

While various descriptions of the present invention are described above, it should be understood that the various features can be used singly or in any combination thereof. Therefore, this invention is not to be limited to only the specifically preferred embodiments depicted herein.

Further, it should be understood that variations and modifications within the spirit and scope of the invention may occur to those skilled in the art to which the invention pertains. Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

What is claimed is:

1. A vertebral bone prosthetic device comprising:
    an interior body, provided with an outer surface and a first coupling element thereon;
    an exterior hollow body with a bore therein extending along a central axis, with the exterior body being configured and dimensioned to be slidably received by the interior body along the central axis, and provided with an interior surface and an exterior surface, the interior surface having a groove; and
    a fixation ring having inner and outer surfaces, with the inner surface having a second coupling element thereon, the fixation ring configured and dimensioned to be received within the groove for rotational movement about the central axis of the exterior body,
    wherein rotation of the fixation ring results in engagement of the first and second coupling elements to thereby prevent relative sliding movement between the interior and exterior bodies.

2. The device of claim 1, wherein the fixation ring is rotatable between first second positions, the first position disengaging the coupling elements and allowing relative sliding movement and the second position engaging the coupling elements and blocking relative sliding movement.

3. The device of claim 2, wherein the first coupling elements consist of elevations and the second coupling elements consist of recesses configured and dimensioned to match the elevations.

4. The device of claim 3, wherein the elevations are restricted to a number of sectors, each of the sectors subtending a first angle and the recesses are restricted to a number of sectors, each of the sectors subtending a first angle, wherein the first and second angles are each less than 360°.

5. The device of claim 4, wherein the first angle equals the second angle.

6. The device of claim 4, wherein the sectors with elevations alternate with substantially smooth sectors.

7. The device of claim 4, wherein the sectors with recesses alternate with substantially smooth sectors.

8. The device of claim 1, wherein the interior body is a hollow-cylindrical body.

9. The device of claim 1, wherein a superior end plate is located on the interior body free end.

10. The device of claim 1, wherein an inferior endplate is located on the exterior body free end.

11. The device of claim 10, wherein each of the end plates has a bone contacting surface configured and dimensioned to rest against a vertebra.

12. The device of claim 11, wherein each bone-contacting surface perforations to enhance bone-in growth.

13. The device of claim 11, wherein each bone-contacting surface has a plurality of projections to enhance interlocking with the vertebrae.

14. The device of claim 1, wherein the exterior body further comprises a channel running along the central axis.

15. The device of claim 14, wherein the inner body further comprises a tab engaging the channel to thereby prevent relative rotation between the inner and outer bodies.

16. The device of claim 1, wherein at least a portion of the groove extends from the interior surface to the exterior surface to form a clearance in the exterior body.

17. The device of claim 16, wherein the fixation ring comprises an offset engaging the clearance and configured and dimensioned for rotation of the fixation ring.

18. The device of claim 17, wherein the offset comprises an axially projecting V-shaped elevation, which detents into matching fluting on the clearance, detachably locking the fixation ring into either the first or second position.

* * * * *

UNITED STATES PATENT AND TRADEMARK OFFICE
CERTIFICATE OF CORRECTION

PATENT NO.    : 6,524,341 B2
DATED         : March 14, 2003
INVENTOR(S)   : Bruno Läng and Alfred Benoit It is certified that error appears in the above-identified patent and that said Letters Patent is hereby corrected as shown below:

Column 6,
Line 47, after "surface" insert -- includes --.

Signed and Sealed this

Fifteenth Day of April, 2003

JAMES E. ROGAN
*Director of the United States Patent and Trademark Office*